United States Patent [19]

Christensen et al.

[11] 4,301,074
[45] Nov. 17, 1981

[54] 6-(1'-HYDROXYETHYL)-2-SUBSTITUTED-PEN-2-EM-3-CARBOXYLIC ACID

[75] Inventors: Burton G. Christensen, Metuchen; Frank P. DiNinno, Old Bridge, both of N.J.

[73] Assignee: Merck & Co., Inc., Rahway, N.J.

[21] Appl. No.: 108,885

[22] Filed: Dec. 31, 1979

Related U.S. Application Data

[60] Division of Ser. No. 948,711, Oct. 10, 1978, Pat. No. 4,260,618, which is a continuation-in-part of Ser. No. 852,275, Nov. 17, 1977, abandoned.

[51] Int. Cl.$^3$ .................................... C07D 499/04
[52] U.S. Cl. ......................... 260/245.2 R; 424/246; 260/239 A
[58] Field of Search ............... 260/245.2 R, 239 A; 424/270

[56] References Cited

U.S. PATENT DOCUMENTS 4,182,711  1/1980  Ueda et al. ...................... 548/178

Primary Examiner—Nicholas S. Rizzo
Attorney, Agent, or Firm—James A. Arno; Hesna J. Pfeiffer

[57] ABSTRACT

Disclosed are 6-(1'-hydroxyethyl)-2-substituted-pen-2-em-3-carboxylic acids of the following structure:

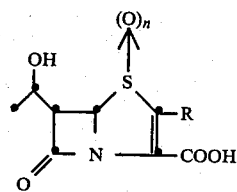

wherein R is, inter alia, hydrogen, —OR, —SR, —NR$_2$, alkyl, aryl, aralkyl, or heterocyclyl; n is 0 or 1; when n=1 R is as defined but not —SR. Such compounds and their pharmaceutically acceptable salt and ester derivatives are useful as antibiotics. Also disclosed are processes for the preparation of such compounds, pharmaceutical compositions comprising such compounds and methods of treatment comprising administering such compounds and compositions when an antibiotic effect is indicated.

1 Claim, No Drawings

6-(1'-HYDROXYETHYL)-2-SUBSTITUTED-PEN-2-EM-3-CARBOXYLIC ACID

This is a division of application Ser. No. 948,711, filed Oct. 10, 1978, now U.S. Pat. No. 4,260,618, which in turn is a continuation-in-part application of U.S. Ser. No. 852,275, filed Nov. 17, 1977, now abandoned.

BACKGROUND OF THE INVENTION

This invention relates to 6-(1'-hydroxyethyl)-2-substituted-pen-2-em-3-carboxylic acids and their pharmceutically acceptable salts and esters, which compounds are useful as antibiotics and which may be represented by the following generic structural formula (I):

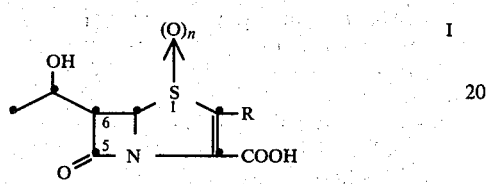

wherein R is, inter alia, hydrogen, —OR, —SR, —NR$_2$, alkyl, aryl, aralkyl, heterocyclyl or heterocyclylalkyl; n=0 or 1; when n=1, then R is as defined but not —SR.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as S. aureus, Strep. pyogenes, and B. subtilis, and gram negative bacteria such as E. coli, Pseudomonas, Proteus morganii, Serratia and Klebsiella. Further objects of this invention are to provide chemical processes for the preparation of such antibiotics and their non-toxic pharmaceutically acceptable salts; pharmaceutical compositions comprising administering such antibiotics and compositions when an antibiotic effect is indicated.

DETAILED DESCRIPTION OF THE INVENTION

The compounds of the present invention (I, above) are conveniently prepared by the following scheme:

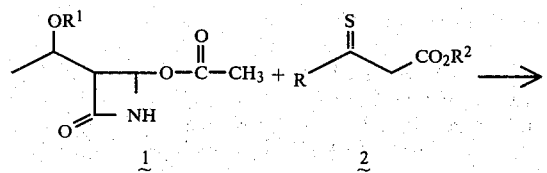

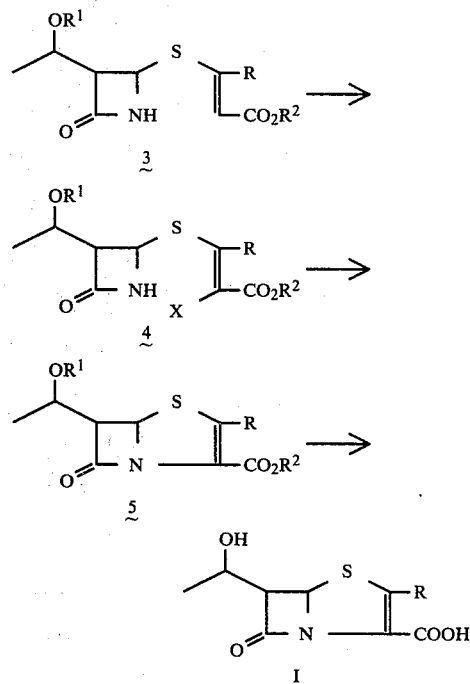

In words relative to the above diagram, the starting azetidinone 1 is treated with a substituted 1-thionoacetate derivative (2) in the presence of a base such as sodium methoxide, aluminum isopropoxide, triethylamine and the like in a solvent such as methanol, methylenechloride, tetrahydrofuran and the like at a temperature of from 0° to 25° C. for from 1 to 100 hours to provide seco-lactam (3). Relative to these reactions, R$^1$ is a readily removable protecting group such as p-nitrobenzyloxycarbonyl, trichloroethoxycarbonyl, t-butyldimethylsilyl or the like; R$^2$ is a readily removable carboxyl blocking group such as p-nitrobenzyl, t-butyl, trichloroethyl or the like; and R is as defined above.

Halogenation of 3 yields 4 wherein X is halo, such as chloro or bromo. Suitable halogenating agents include N-chlorosuccinimide, N-bromosuccinimide, N-bromoacetamide and the like; and the reaction 3→4 is conducted in the presence of the halogenating agent of choice in a solvent such as tetrahydrofuran, benzene, benzene-ether and the like at a temperature of from −78° C. to 60° C. for from 0.5 to 2 hours. Cyclization of 4 to provide 5 is accomplished by treating 4 with a strong base such as lithium diisopropylamide, lithium hexamethyldisilazide, lithium tetramethylpiperdide or the like in a solvent such as tetrahydrofuran, dimethoxyethane, diethylether or the like in the presence of a metal complex coupling agent at a temperature of from −78° C. to 22° C. for from 0.5 to 18 hours; suitable metals include Cu(I); the platinum metals such as Pd°; Ni°, Ni(II) and the like; representative complexes include cuprous iodide, cuprous bromidedimethyl sulfide complex, cuprous iodide-tri-n-butylphosphine complex, tetrakistriphenylphosphine palladium (0), tetrakistriphenylphosphine nickel (0), bis-cyclooctadienyl nickel (0), bis(diphenylphosphino)ethane-nickel (II) dichloride, or the like. The fully protected intermediate 5 is deblocked to provide I. When the preferred blocking groups are employed, that is, R$^1$ is p-nitrobenzyloxycarbonyl or trichloroethoxycarbonyl and R$^2$ is p-nitrobenzyl or trichloroethyl, the deblocking reaction may be accomplished by hydrogenation or zinc mediated reduction according to well-known procedures. A representative deblocking procedure comprises treating 5 in a solvent such as ethylacetate under hydrogen (1–40 atmospheres) at a temperature of 0° to 22° C. for from 0.25 to 2 hours in the presence of a hydrogenation catalyst such as 10%/Pd/C, 5%Pd/BaCO₃, 5%Pt/C or the like.

The starting azetidinone material 1 may conveniently be prepared by the following scheme:

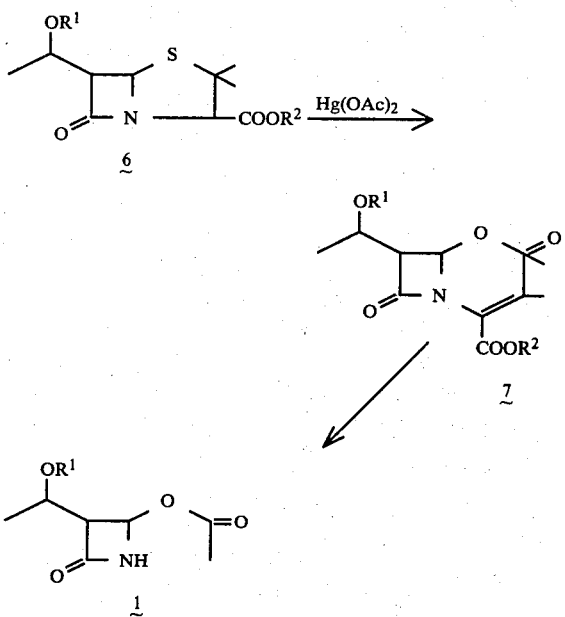

wherein R¹ and R² are as defined above; the preparation of starting material 6 (R¹=H) is described in the literature: F. DiNinno, et al., *J. Org. Chem*, 42, 2960(1977).

In words relative to the above diagram, starting material 6 is cleaved with mercuric acetate (Hg(OAc)₂) in acetic acid solution at a temperature of from 22° C. to 110° C. for from 0.25 hours to 8 hours to provide the acetoxy lactam 7. Relative to these reactions, R¹ is a readily removable protecting group such as p-nitrobenzyloxycarbonyl, trichloroethoxycarbonyl, t-butyldimethylsilyl or the like; R² is a selected carboxyl protecting group such as methyl, benzyl, trichloroethyl or the like. Removal of the isopropylidene ester function is accomplished by treating 7 with potassium permanganate, osmium tetroxide or the like in a solvent such as aqueous pyridine, aqueous acetone or the like at a temperature of 0° to 22° C. for from 0.25 to 2 hours, to provide azetidinone 1. Analogous procedures are known in the literature; see, for example: E. G. Brain, et al., *J. Chem. Soc., Perkin I*, 447 (1976); R. J. Stoodley and N. R. Whitehouse, Ibid., 32 (1973).

Starting material 2, in the above-described synthesis, may conveniently be prepared in a variety of ways. One preferred method, when the ultimate 2-substituent (Structure I) is —SR, is shown in the following scheme:

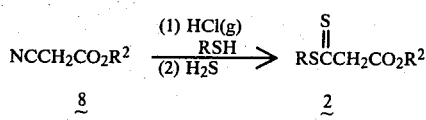

In words relative to the above diagram, the cyanoacetic acid ester 8 is treated with gaseous hydrogen chloride in a solvent such as benzene, diethylether, tetrahydrofuran or the like in the presence of a mercaptan (RSH) at a temperature of from 0° C. to 25° C. for from 0.25 to 1 hour. The resulting mixture is stirred at a temperature of from 0° to 80° C. for from 8 to 96 hours. The precipitate formed is collected by filtration and is dissolved in anhydrous dimethylsulfoxide or dimethylformamide or the like. The mixture is treated with gaseous hydrogen sulfide at a temperature of from 0° C. to 25° C. for from 10 min. to 24 hours and is stirred further at a temperature of from 0° C. to 25° C. for from 2 to 24 hours to provide 2. Relative to these reactions R and R² are as previously defined.

The following list representatively illustrates suitable starting materials 2. Such reagents are employed as described in the above procedure to provide species bearing a preferred substituent at the 2-position.

| | R | R² |
|---|---|---|
| (1.) | ![triazole with CH₃] N—N / N=N(CH₃) | —CH₂—C₆H₄—NO₂ |
| (2.) | CH₃ | " |
| (3.) | phenyl | " |
| (4.) | pyridyl | " |
| (5.) | thienyl | " |
| (6.) | furyl | " |
| (7.) | —CH₂—C₆H₄—CH₂NCO₂PNB / H | " |
| (8.) | CH₂NHCOCH₂—C₆H₄—NO₂ | " |
| (9.) | CH₂CH₂OAc | " |
| (10.) | CH₂CH₂OSi(CH₃)₂[C(CH₃)₃] | " |
| (11.) | N—N / N=N(CH₃) triazole | —CH₂OCOC(CH₃)₃ |

When starting material 2, in the above-described synthesis, provides the 2-substituent as —R, it may be prepared by known literature procedures: F. Duus, et al., *Ark. Kemi*, 29, 191 (1968); Chem. Abs., 69:3140p (1968).

A schematic summary of such a convenient process is given below:

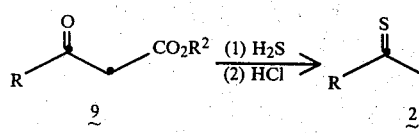

In words relative to the above diagram, the readily available substituted 3-ketoproprionic acid ester derivatives 9 is treated with hydrogen sulfide gas for from 1 to 3 hours in a solvent such as acetonitrile, dimethylformamide, dimethylsulfoxide or the like at a temperature of from −60° to 25° C. The mixture is then treated with gaseous hydrogen chloride for from 0.5 to 2 hours at a temperature of from −60° to 25° C. to provide starting material 2. Relative to this reaction, R and $R^2$ are as previously described.

The following list representatively illustrates suitable starting materials 2. Such reagents are employed as described in the above procedure to provide species bearing a preferred substituent at the 2-position.

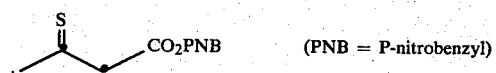 (PNB = P-nitrobenzyl)

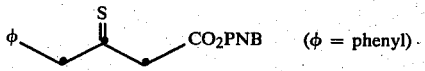 (φ = phenyl)

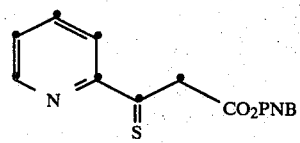

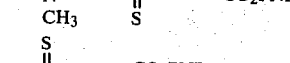

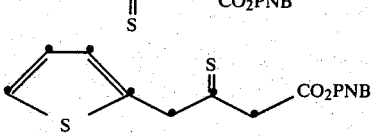

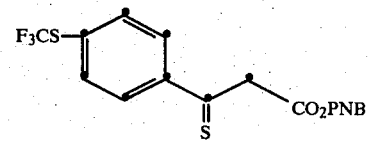

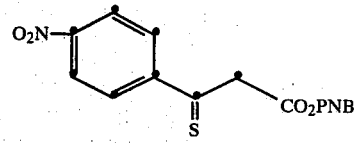

An alternative procedure, which is especially suitable for embodiments wherein R is as defined, but not —OR, —SR, or —NR₂, is illustrated below:

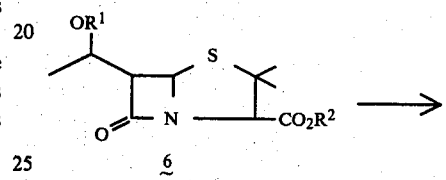

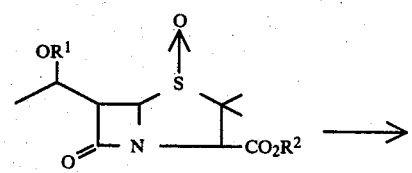

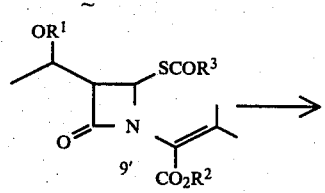

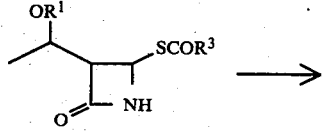

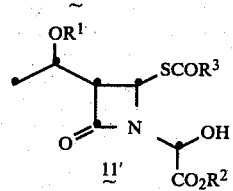

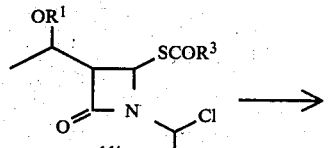

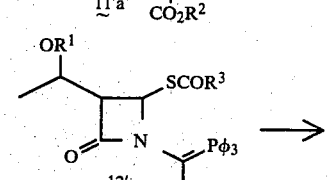

wherein all symbolism is as previously defined; R is aryl such as phenyl and substituted phenyl; φ is phenyl.

In word relative to the above reaction diagram, above-defined starting material 6 is taken through the scheme 6→→12' whereupon 12' is converted to above-defined species 5 which is deblocked as previously described to yield I. The oxidation reaction 6→8' is known and is conveniently accomplished by treating 6 in a solvent such as methylene chloride, chloroform, benzene, tetrahydrofuran or the like at a temperature of from −78° −25° C. with a stoichoimetric amount of an oxidizing agent such as m-chloroperbenzoic acid, perbenzoic acid, hydrogen peroxide, peracetic acid or the like. The resulting sulfoxide 8', after isolation by conventional work-up, in a solvent such as benzene, toluene, dioxane, or the like is treated with a stoichiometric to slight excess of a phosphine such as tri-n-butylphosphine, trimethylphosphite, triphenylphosphite, or the like, and a stoichiometric to ten-fold excess of the anyhydride $(R^3CO)_2O$ (for example, substituted or unsubstituted benzoic anhydride). The mixture is typically heated under nitrogen for from 0.5 to 50 hours at a temperature of from 50° C. to reflux to yield 9', which may be isolated by conventional work-up. In cases where the isomerization of the β,γ-unsaturated ester to the α,β-unsaturated ester does not occur under the reaction conditions or during work-up the product is conveniently isomerized to the latter (as in 9') with triethylamine. Cleavage of 9' to provide 10' is typically accomplished by treating 9', in a solvent such as 8:1 acetone-water, aqueous pyridine, or the like with an equivalent to three-fold excess amount if an oxidizing agent such as potassium permanganate, osmium tetroxide, sodium periodate or the like at a temperature of from 0° to 25° C. for from 5 min. to 2.0 hr., after which the reaction is quenched and 10' isolated by conventional work-up. The reaction 10'→11' is accomplished by treating 10 with an excess of glyoxalate ester such as p-nitrobenzyl-glyoxalate hydrate. The reaction is conveniently carried out in a solvent such as benzene, toluene, xylene or the like at a temperature of from about 25° C. to reflux under a nitrogen atmosphere for from about 2 to 10 hours. The reaction 11'→11'a→12' may be conducted stepwise. The halogenation reaction 11'→11'a may be conducted by any of a variety of well-known halogenation means. Suitable reagents include: $SOCl_2$, $POCl_3$, oxalyl chloride an the like. A preferred means of chlorination involves treating 2 in a solvent such as tetrahydrofuran (THF), ether, $CH_2Cl_2$ and the like with thionylchloride in the presence of 1 to 2 equivalents (relative to the thionylchloride) of a base such as pyridine, triethylamine, quinoline and the like. Typically, the reaction is conducted at a temperature of from −30° to 25° C. for from 0.5 to 1 hr. The resulting species, 11'a, is isolated, if desired, by conventional procedures for later reaction, 11'a→12'. The intermediate 12' is prepared from 11'a by treating 11'a in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2-cyanoethyl)-phosphine or the like. Typically, the reaction is conducted under a nitrogen atmosphere at a temperature of from −20° to 25° C., for from 0.5 to 2 hrs. The closure reaction 12'→5 is accomplished by heating the phosphoraneazetidinone 12' in a solvent such as benzene, toluene, dioxane, xylene, DMF or the like at a temperature of from 20° to 120° C. for from 0.25 hrs. to 5 days. The resulting penem is deblocked to yield I according to the previously described procedure.

In the generic representation of the compounds of the present invention (I):

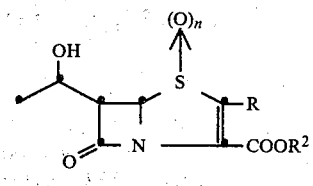

The preferred values for R are: hydrogen; substituted and unsubstituted: —OR, —SR, —NR₂ (R is defined herein); alkyl having 1–6 carbon atoms, aryl such as phenyl, aralkyl wherein the aryl moiety is preferably phenyl and the alkyl has 1–6 carbon atoms such as benzyl, phenethyl and the like, heterocycyl or hetereocyclyalky wherein the alkyl has 1–3 carbon atoms and the heterocyclic ring comprises 4–6 atoms, up to 4 of which may be selected from oxygen, sulfur and nitrogen; and wherein the chain or nuclear substituent on R is selected from: amino, mono-, di- and trialkylamino, hydroxyl, alkoxyl, mercapto, alkylthio, arylthio such as phenylthio, sulfamoyl, amidino, guanidino, nitro, chloro, bromo, fluoro, cyano and carboxyl; the alkyl moieties of the above-recited substituents have 1–6 carbon atoms. The preferred value of n is 0.

Especially preferred embodiments of the present invention are those, as defined above, except that any unsubstituted amino group borne on radical R of Structure I is derivatized according to the teachings of Belgium Pat. No. 848,545 (issued May 20, 1977); the resulting amino group being represented thusly (partial structure):

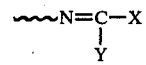

wherein X and Y are defined by the publication; species wherein X is H or lower alkyl and Y is $NH_2$ are especially preferred.

The preferred ester moieties, $R^2$, (see 5, above) used as carboxyl protecting groups are those wherein $R^2$ is benzyl, p-nitrobenzyl, o-nitrobenzyl, t-butyl, bromo-t-butyl, t-butyl-dimethylsilyl, trimethylsilyl, trichloroethyl; $R^2$ may also represent, in addition to hydrogen, pharmaceutically acceptable ester moieties such as pivaloyloxymethyl, allyl, methallyl, (2-methylthio)-ethyl, or 3-buten-1-yl; and pharmaceutically acceptable salt cations.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, diloweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative examples include salt derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

The salts can be mono-salts such as the mono- sodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel 6-(1'-hydroxyethyl)-2-substituted-pen-2-em-3-carboxylic acids of the present invention are valuable antimicrobial substances which are active against various gram-positive and gram-negative pathogens. Thus, the free acid and especially the salts thereof such as amino and metal salts, particularly the alkali metals and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixers and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa,* Pseudomonas and *Bacterium proteus.* The anti-bacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These anti-biotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica, disintegrants, for example, potato starch or acceptable wetting agents such as sodium lauryl sulphate. The tablets may be coated according to methods well known in the art. Oral liquid preparation may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydrocyethylcellulose, carboxymethyl cellulose, aluminum stearate gel or hydrogenated edible oils, for example almond oil, fractionated coconut oil, oily esters, propylene glycol, or ethyl alcohol: preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All temperatures are given in °C.

EXAMPLE 1

Preparation of Azetidinone 1

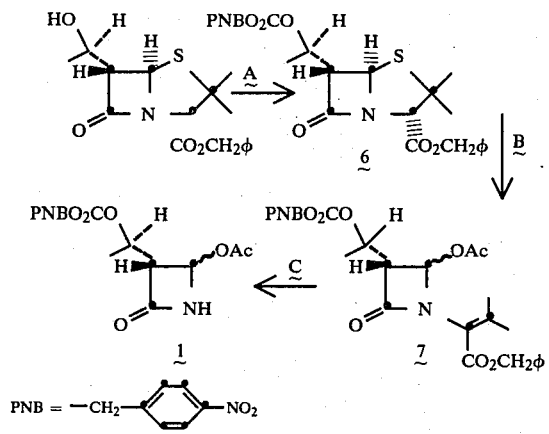

Step A
Preparation of 6

To a stirred solution of 215 mg. (0.6 mmol) of benzyl-6α-[(R)-1'-hydroxyethyl]penicillanate and 276 mg (0.13 mmol) p-nitrobenzylchloroformate in 5 ml dry methylene chloride at 0° C. is added in one portion solid 4-dimethylaminopyridine (156 mg., 0.13 mmole). The mixture is stirred at 0° C. under a nitrogen atmosphere for 2 min. and allowed to warm over 28 min. The mixture is poured into ice-H$_2$O and extracted with CH$_2$Cl$_2$. The organic phase is separated and washed successively with cold, dilute, aqueous HCl and saturated NaCl (aq.). After drying with MgSO$_4$, the filtered solution is evaporated and dried in vacuo to give 420 mg. of residue. Purification by plate layer chromatography [1 development C$_6$H$_6$—EtOAc(9:1)] provides 278.2 mg. (84%) of product 6; ir (CHCl$_3$) 1770, 1740 cm; nmr (CDCl$_3$) 1.4, 3H(S); 1.48, 3H(d, J=6 Hz); 1.61, 3H(S); 3.46, 1H(dd, J=2, 7 Hz); 4.5, 1H(S); 5.2, 2H(S); 5.23, 1H(m); 5.27, 2H(S); 5.31, 1H(d, J=2 Hz); 7.37, 5H(S); 7.53, 2H(D, J=8 Hz); 8.32, 2H(d, J=8 Hz).

Step B
Preparation of 7

A stirred mixture of 186.8 mg (0.36 mmol) of 6 and 232 mg. (0.73 mmol) Hg (OAc)$_2$ (mercuric acetate) in 7 ml glacial HOAc (acetic acid) is heated at 90° C. for 1.5 hour under a nitrogen atmosphere. The cooled mixture is filtered through supercel, washing thoroughly with CH$_2$Cl$_2$. The filtrate is diluted with H$_2$O and is neutralized with solid NaHCO$_3$. The mixture is extracted thoroughly with CH$_2$Cl$_2$ and the combined extracts are washed successively with saturated NaHCO$_3$ (aq.) and saturated NaCl (aq.). After drying with MgSO$_4$, the filtered solution is evaporated and the residue so obtained is purified by plate layer chromatography [1 development CHCl$_3$—EtOAc (20:1)] to provide 138.6 mg (71%) of approximately a 1:1 mixture of cis and trans-acetoxyazetidinones 7; ir (CHCl$_3$) 1770, 1750, 1730; nmr (CDCl$_3$) 1.4 and 1.53, 3H(d's, J's=6 Hz and 7 Hz); 1.86, 1.96, & 2.0, 6H(S); 2.23, 3H(S); 3.4 & 3.58, 1H(dd's, J's=2,7 Hz & 4,10 Hz); 5.2, 1H(m); 5.2, 2H(S); 5.23, 2H(S); 6.23 & 6.3, 1H(d's, J's=2 & 4 Hz); 7.3, 5H(S); 7.53, 2H(d, J=8 Hz); 8.2, 2H(J=8 Hz); mass spectrum m/e 540(M+), 498, 390, 346, 301, 222, 210, 193, 136, 91.

Step C
Preparation of 1

To a stirred solution of 138.6 mg (0.26 mmol) of azetidinones 7 in 3.5 ml of 8:1 (CH$_3$)$_2$CO—H$_2$O and 1 drop of pH 7 0.1 N phosphate buffer at room temperature (25° C.) is added 40.6 mg (0.26 mmol) of solid KMnO$_4$. The mixture is stirred under a nitrogen atmosphere at 25° C. for 8 min. After this time, 40.6 mg (0.26 mg (0.26 mmol) of additional KMnO$_4$ is added and the mixture is stirred further for 45 min. The reaction mixture is diluted with EtOAc (ethylacetate) and treated with cold, aqueous Na$_2$S$_2$O$_3$ until the violet coloration of KMnO$_4$ is no longer apparent. The mixture is filtered through celite and is washed well with EtOAc. The filtrate is washed with saturated NaCl (aq.), dried (MgSO$_4$), filtered, and evaporated. Purification of the residue by plate layer chromatography [1 development CHCl$_3$—EtOAc(3:1)] gives 65.5 mg. (72%) of the azetidinone mixture 1; ir (CHCL$_3$) 3300, 1785, 1750 cm$^{-1}$; nmr (CDCl$_3$), 1.5 & 1.53, 3H(d's, J's=7 Hz); 1.98 & 2.12, 3H(S); 2.43, (dd, J=2, 6 Hz) & 2.65, (dq,J=1.5, 4.0, 9 Hz) [1H]; 5.28, 2H(S); 5.3, 1H(M); 5.88 & 5.95, 1H (d's, J's=1.5 & 4.0 Hz); 6.93, 1H(bs); 7.57, 2H(d, J=8 Hz); 8.25, 2H(d, J=8 Hz); mass spectrum m/e 309, 292, 249, 181, 154, 136.

EXAMPLE 2

Preparation of $\overset{S}{\overset{\|}{R}SCCH_2CO_2R^2}$ (2); R = CH$_3$,
R$^2$ = PNB (p-nitrobenzyl)

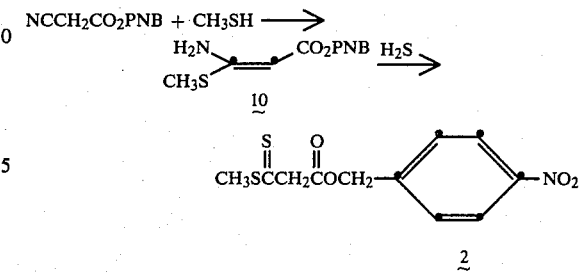

To a stirred mixture of 11.0 g (0.05 mol) of p-nitrobenzylcyanoacetate and 3.72 g (0.078 mol) methylmercaptan in 200 ml of sodium dried benzene at 25° C. is introduced a stream of HCl(g) until 1.85 g (0.05 mmol) is added. The mixture is then stirred at 25° C. under nitrogen atmosphere for 74.5 hrs. The solution is decanted away from the separated solid and the moist precipitate is dissolved in 50 ml of dry pyridine. (Alternatively the precipitate is dissolved in dry dimethylfulfoxide and treated with H₂S(g) as described below to afford 2 directly.) The pyridine solution is treated with excess H₂S(g) and is stirred at 25° C. under nitrogen atmosphere for 2 hrs. The reaction mixture is poured into ice/water and extracted with ether. The separated extract is washed twice with water and twice with brine solution then dried over MgSO₄, filtered, and evaporated to give a crystalline mass. Recrystallization from ether gives 5.0 g of the enamide 10; ir(CHCl₃), 3636, 3322, 1664, 1592, 1517 cm⁻¹; NMR(CDCl₃) δ: 2.4(s, 3H), 4.68 (s, 1H); 5.17 (s, 2H); 6.43 (bs, 2H); 7.43 (d, J=8 Hz, 2H); 8.13 (d, J=8 Hz, 2H); mass spectrum m/e 268 (M+), 221, 175, 136. Purification of the mother liquors from above by column chromatography on silica gel eluting with CHCl₃-pet-ether (1:1) provides 940 mg of 2 as an orange oil: ir (CHCl₃) 1742, 1613, 1522; NMR(CDCl₃) δ2.67 (s, 3H); 4.13 (s, 2H); 5.23 (s, 2H); 7.47 (d, J=9 Hz, 2H); 8.17 (d, J=9 Hz, 2H); mass spectrum m/e 285 (M+), 238, 136, 106. The enamide 10 is converted to 2 by the following procedure.

The crude enamide 10 7.9 g (29 mmol) is dissolved in 40 ml of dry DMF (dimethylformamide) at 25° C. and is treated successively with 3.7 g (32 mmol) of trifluoroacetic acid and excess hydrogen sulfide. The resulting mixture is stirred magnetically at 25° C. under CaCl₂ drying tube protection for 5 hrs. The mixture is poured into 75 ml ice-H₂O and extracted with 100 ml Et₂O (diethylether). The separated etheral extract is washed twice with H₂O and saturated NaCl(aq) solution, then dried with MgSO₄, filtered, and evaporated. Purification by column chromatography on silica gel eluting with CHCl₃-petroleum ether (1:1) gives 6.55 g (74%) of 2.

EXAMPLE 3

Preparation of dithioate derivative 2, RSCCH₂CO₂R², $$\overset{S}{\underset{}{\|}}$$

$$\overset{O}{\underset{}{\|}}$$

(R = CH₂CH₂OCCH₃; R² = PNB)

To a stirred mixture of 6.78 g (5.6 mmol) of 2-acetoxyethyl mercaptan and 11.0 g (5 mmol) p-nitrobenzylcyanoacetate in 100 ml of dry benzene is introduced 3.0 g (8.1 mmol) 1f hydrogen chloride gas. The mixture is stirred under N₂ at RT (25° C.) for 42 hours after which time the solution is decanted away from the oily mass. The mass is washed twice with dry benzene by decantation. The oil is dissolved in 20 ml of dry dimethylformamide and is treated with a vigorous stream of hydrogen sulfide (g) for 5 min. The mixture is stirred at 25° C. for 5 hours and then is poured into ice cold water and is extracted with ether. The ether extract is washed well with water, then brine, and is dried over MgSO₄, filtered, and evaporated. Purification by column chromatography on silica gel provides the dithioate derivative 2 as an orange solid; ir (CHCl₃) 1770, 1600, 1538 cm⁻¹; nmr (CDCl₃) δ: 2.03 3H(s); 3.53, 2H(t, J=6 Hz); 4.1, 2H(s); 4.27, 2H(t, J=6 Hz); 5.25, 2H(s); 7.46, 2H(d, J=9 Hz); 8.2, 2H(d, J=9 Hz); mass spectrum m/e 357 (M+), 297, 271, 206, 169, 136.

EXAMPLE 4

Preparation of Benzyl-thiobenzoylacetate 2, $\overset{S}{\underset{}{\overset{\|}{R C}}}$CH₂CO₂R²

(R = phenyl; R² = benzyl):

Into a stirred solution 19.2 g of benzylacetoacetate in 150 ml of acetonitrile at −60° C. is passed a stream of hydrogen sulfide gas for 1.5 hours, followed by dry HCl(g) for 40 min. The reaction solution is then let warm to −20° C. and is poured into ice water. The product 2 is extracted into benzene and purified by vacuum distillation to provide the known benzyl-thiobenzoylacetate, bp 98° (0.05 mm).

EXAMPLE 5

Following the procedure described in the foregoing text and Examples, the following starting reagents 2 necessary for the preparation of the compounds of the present invention are representatively obtained by analogy.

2

| Compound | R | R² |
|---|---|---|
| (1.) | 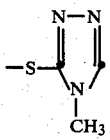 |  |
| (2.) | —SCH₃ | " |
| (3.) | 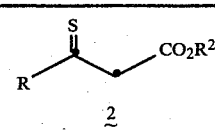 | " |
| (4.) | 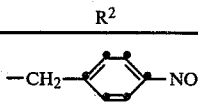 | " |
| (5.) |  | " |
| (6.) |  | " |

-continued

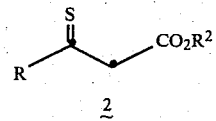

| Compound | R | R² |
|---|---|---|
| (7.) | —SCH₂—⌬—CH₂NHCOPNB (O=) | " |
| (8.) | —SCH₂NHCOOCH₂—⌬—NO₂ (O=) | " |
| (9.) | —SCH₂CH₂OCCH₃ (O=) | " |
| (10.) | —SCH₂CH₂OSi(CH₃)₂C(CH₃)₃ | " |
| (11.) | phenyl | benzyl |
| (12.) | methyl | p-nitrobenzyl |
| (13.) | 2-furyl | " |
| (14.) | 2-thienyl | " |
| (15.) | 2-pyridyl | " |
| (16.) | 2-N-methyltetrazolyl | " |
| (17.) | benzyl | " |
| (18.) | 2-thiatriazolyl | " |
| (19.) | p-trifluoromethylthiophenyl | " |
| (20.) | p-nitrophenyl | " |
| (21.) | 2-thienylmethyl | " |

EXAMPLE 6

Preparation of secolactam $\underset{\sim}{3}$ (R₁=R₂=PNB, R=SCH₃)

[reaction scheme showing azetidinone 1 + dithiomalonate 2 → secolactam 3]

PNB = p-nitrobenzyl

To a stirred mixture of 70.4 mg (0.2 mmol) of azetidinones $\underset{\sim}{1}$ and 57.0 mg (0.2 mmol) of dithiomalonate derivative $\underset{\sim}{2}$ in 2 ml of dry tetrahydrofuran (THF) at 25° C. is added 57.2 mg (0.28 mmol) of solid aluminum isopropoxide. The mixture is stirred at 25° C. under nitrogen atmosphere for 24 hours and is then partitioned between ethylacetate and cold, dilute aqueous HCl. The EtOAc phase is separated, washed with brine, dried with MgSO₄, filtered, and evaporated. Purification by plate layer chromatography provides seco-lactam 3.

EXAMPLE 7

Following the procedures described in the foregoing Examples and text, the following secolactams $\underset{\sim}{3}$ are prepared by analogy.

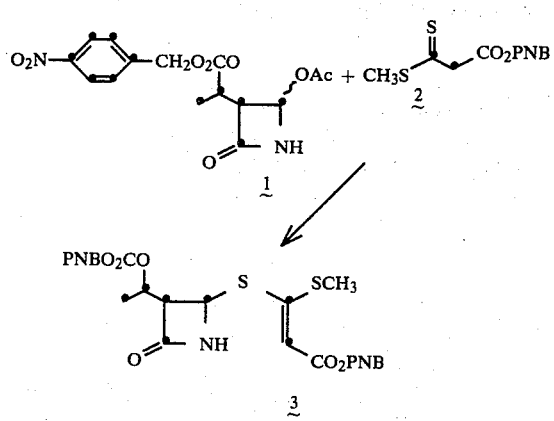

| Compound | R |
|---|---|
| (1.) | —CH₂CH₃ |
| (2.) | [N-methyltetrazolyl] |
| (3.) | [furyl] |
| (4.) | [pyridyl] |
| (5.) | [furyl] |
| (6.) | [thienyl] |
| (7.) | —CH₂—⌬—CH₂NCO₂PNB (H) |
| (8.) | —CH₂NCOCH₂—⌬—NO₂ (O=, H) |
| (9.) | —CH₂CH₂OCCH₃ (O=) |
| (10.) | —CH₂CH₂OSi (CH₃)₂C(CH₃)₃ |
| (11.) | —⌬—CH₂NCO₂PNB (H) |

EXAMPLE 8

Preparation of secolactam 3

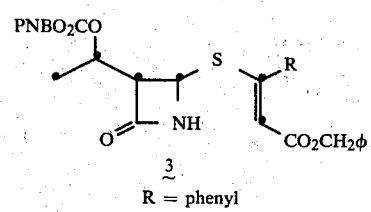

R = phenyl

To a stirred mixture of 35.2 mg (0.1 mmol) of azetidinones 1 and 27 mg (0.1 mmol) of benzylthiobenzoylacetate in 2.0 ml methanol at 25° C. is added 59.4 mg (0.11 mmol) of sodium methoxide. The mixture is stirred at 25° C. under a nitrogen atmosphere for 24 hours. The solvent is removed by evaporation and the residue is partitioned between ethyl acetate and cold water. The EtOAc phase is separated, washed with brine, dried with MgSO$_4$, filtered and evaporated. The secolactam 3 is obtained by plate layer chromatography.

EXAMPLE 9

Employing the procedures described in the foregoing text and Examples, the following azetidinones 3 are prepared by analogy:

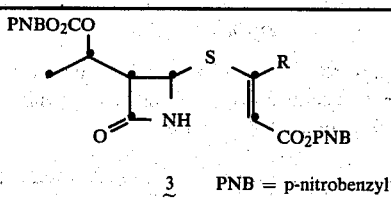

3  PNB = p-nitrobenzyl

| Compound | R |
|---|---|
| (1.) | O$_2$N—⟨phenyl⟩—CH$_2$OC(O)NHCH$_2$—⟨phenyl⟩— |
| (2.) | —CH$_3$ |
| (3.) | thienyl |
| (4.) | furyl |
| (5.) | pyridyl |
| (6.) | N-methyl tetrazolyl |
| (7.) | benzyl |
| (8.) | thiadiazolyl |
| (9.) | CF$_3$S—⟨phenyl⟩— |
| (10.) | O$_2$N—⟨phenyl⟩— |
| (11.) | thienyl—⟨phenyl⟩— |

EXAMPLE 10

Preparation of bromide 4

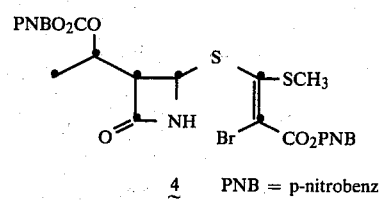

4  PNB = p-nitrobenzyl

To a stirred solution of the secolactam 3 prepared in Example 6 (57.7 mg 0.1 mmol) and 17.9 mg (0.1 mmol) of hexamethylphosphoramide in 2 ml dry tetrahydrofuran at 25° C. is added 17.8 mg (0.1 mmol) of N-bromosuccinimide. The mixture is stirred at 25° C. under N$_2$ for 0.5 hr. and the solvent is removed under reduced pressure. Purification by repetitive plate layer chromatography affords bromide 4.

EXAMPLE 11

Following the procedures described in the foregoing text and Examples, the following intermediate species 4 are representatively prepared by analogy.

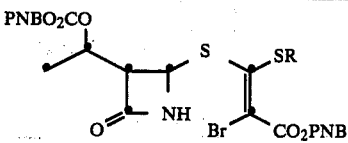

4

| Compound | R |
|---|---|
| (1.) | —CH$_2$CH$_3$ |
| (2.) | furyl |
| (3.) | —CH$_2$—⟨pyrrolyl⟩—CH$_2$NCO$_2$PNB<br>H |
| (4.) | N-methyl tetrazolyl |
| (5.) | furyl |
| (6.) | thienyl |
| (7.) | —CH$_2$CH$_2$OC(O)CH$_3$ |
| (8.) | —CH$_2$CH$_2$OSi(CH$_3$)$_2$C(CH$_3$)$_3$ |
| (9.) | pyridyl |
| (10.) | —CH$_2$NCO$_2$PNB<br>H |

EXAMPLE 12

Preparation of bromide 4

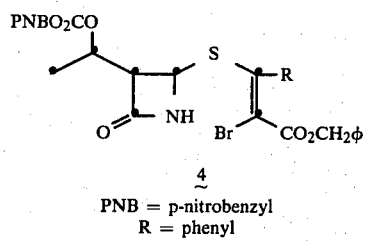

PNB = p-nitrobenzyl
R = phenyl

To a stirred mixture of the secolactam derivative 3 of Example 8 (56.2 mg, 0.1 mmol) and 17.9 mg (0.1 mmol) of hexamethylphosphoramide in 2 ml dry tetrahydrofuran at 25° C. is added 17.8 mg (0.1 mmol) of N-bromosuccinimide. The mixture is stirred at 25° C. under N₂ for 1.0 hour and the solvent removed under reduced pressure. Purification by repetitive plate layer chromatography provides bromide 4.

EXAMPLE 13

Following the procedure described in the foregoing text and Examples, the following bromides 4 are representatively obtained:

| Compound | R |
|---|---|
| (1.) | —⟨phenyl⟩—CH₂NHCCF₃ (=O) |
| (2.) | CH₃ |
| (3.) | (furyl) |
| (4.) | (thienyl) |
| (5.) | (pyridyl) |
| (6.) | N—N / ‖ / N—N-CH₃ (tetrazolyl-CH₃) |
| (7.) | —CH₂—⟨phenyl⟩ |
| (8.) | N—N / ‖ / N—S (thiadiazolyl) |
| (9.) | CF₃S—⟨phenyl⟩— |
| (10.) | O₂N—⟨phenyl⟩— |
| (11.) | (thienyl) |

EXAMPLE 14

Preparation of Penem 5

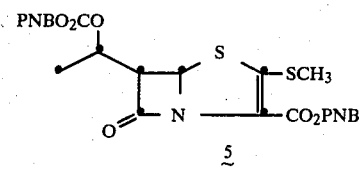

To a stirred mixture of the seco lactam bromide 4 of Example 10 (65.6 mg, 0.1 mmol) and cuprous bromide-dimethylsulfide complex (67.7 mg, 0.33 mmol) in 10 ml dry tetrahydrofuran at −78° C. under a nitrogen atmosphere is added a cold, freshly prepared solution of lithium diisopropylamide (0.11 mmol) in 4 ml dry tetrahydrofuran. The mixture is stirred at −78° C. for 40 minutes and is allowed to warm to 0° C. over a period of 5 hours. At 0° C., 2 ml of saturated ammonium chloride (aq.) solution is added and the mixture is partitioned between ether and water. The organic phase is separated and washed further with saturated ammonium chloride solution and brine. The organic phase is separated, dried over MgSO₄, filtered, and evaporated. Purification is accomplished by plate layer chromatography to yield penem 5.

EXAMPLE 15

Following the procedure described in the foregoing Examples and text, there is obtained the following representative penems 5 by analogy:

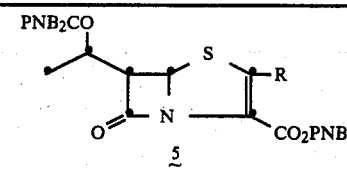

| Compound | R |
|---|---|
| (1.) | —SCH₂CH₃ |
| (2.) | —S—⟨phenyl⟩ |
| (3.) | —SCH₂—⟨phenyl⟩—CH₂NCO₂PNB (H) |
| (4.) | N—N / —S-⟨ / N-N ⟩ / N-CH₃ (triazole) |
| (5.) | —S—⟨furyl⟩ |
| (6.) | —S—⟨thienyl⟩ |
| (7.) | —SCH₂CH₂OCCH₃ (=O) |
| (8.) | —SCH₂CH₂OSi(CH₃)₂C(CH₃)₃ |
| (9.) | —S—⟨pyridyl⟩ |
| (10.) | —SCH₂NCO₂PNB (H) |

-continued

| Compound | R |
|---|---|
| (11.) | phenyl |
| (12.) | CH₃ |
| (13.) | furyl |
| (14.) | thienyl |
| (15.) | pyridyl |
| (16.) | N-methyltetrazolyl |
| (17.) | CH₂—⌬—CH₂NCO₂PNB, H |
| (18.) | thiadiazolyl |
| (19.) | CF₃S—⌬— |
| (20.) | O₂N—⌬— |
| (21.) | thienyl |
| (22.) | —⌬—CH₂NCO₂PNB, H |

EXAMPLE 16

Preparation of penum I

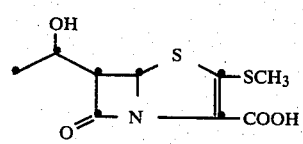

A mixture of 10 mg of 10% palladium on carbon, 5 mg. (0.0086 mmol) of the penem of Example 14 and 1 mg. sodium bicarbonate in 0.8 ml ethylacetate, 0.2 ml isopropanol, and 0.5 ml of 0.5 M pH 7 phosphate buffer is hydrogenated at 40 psi at 25° C. in a Parr shaker for 48 minutes. The catalyst is removed by filtration through supercel and is washed thoroughly with deionized water. The cold filtrate is extracted with ethylacetate and the separated aqueous phase is acidified at 0° C. with 0.1 M pH 2 phosphate buffer to pH 2.5. The aqueous phase is extracted thoroughly with EtOAc. The extracts are combined, dried over anhydrous sodium sulfate, filtered and evaporated to provide penem I.

The free acid is converted to the corresponding sodium salt by treatment with an equivalent amount of an aqueous acetone solution of sodium bicarbonate, followed by removal of the acetone under reduced pressure and lyophilization of the aqueous solution.

In cases where the deblocking procedure results in the formation of zwitterionic penems I, the above acidification is performed as described but is stopped at pH 7. The zwitterionic product is then obtained after chromatography on X-AD-2 resin.

EXAMPLE 17

Preparation of Sodio-6-[1'-Hydroxyethyl]-2-pen-2-em-3-carboxylate

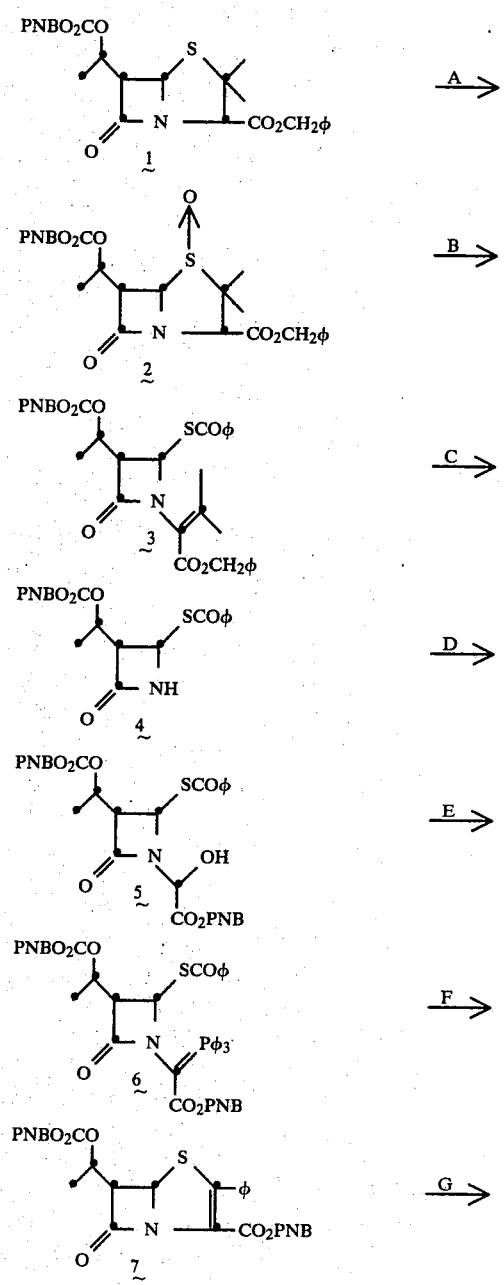

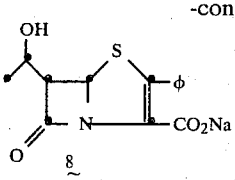

Step A:

To a stirred solution of benzyl-6α-[1'-p-nitrobenzyloxycarbonyloxyethyl]penicillanate (643 mg, 1.25 mmoles) in 15 ml. methylene chloride at 25° C. is added all at once 253.8 mg (1.25 mmoles) of 85% m-chloroperbenzoic acid. The mixture is stirred under an atmosphere of nitrogen at 25° C. for 15 min and is then partitioned between ethyl acetate and ice cold, aqueous sodium bicarbonate solution. The organic phase is separated, washed further with saturated, aqueous sodium chloride solution, dried (MgSO$_4$), filtered, and evaporated. The residue is purified by plate layer chromatography (PLC) [development CH$_2$Cl$_2$—EtOAc (9:1)] to give 326.3 mg (49%) of the desired product as a colorless oil; IR(CHCl$_3$) 1790 and 1750 cm$^{-1}$; NMR(CDCl$_3$) δ:1.1 (S, 3H), 1.53 (d, J=6 Hz, 3H), 1.65 (S, 3H), 3.78 (dd, J=2 and 7 Hz, 1H), 4.53 (s, 1H), 4.97 (d, J=2 Hz, 1H), 5.24 (m, 5H), 7.37 (S, 5H), 7.57 (d, J=8 Hz, 2H), and 8.25 (d, J=8 Hz, 2H).

Step B:

A stirred mixture of 107.2 mg (0.2 mmoles) of the sulfoxide obtained in Step A, 49 mg (0.24 mmoles) of tri-n-butylphosphine, and 229 mg (1.0 mmoles) of benzoic anhydride in 3.0 ml of benzene is refluxed at 90° C. under a nitrogen atmosphere for 7.0 hours. The cooled mixture is partitioned between ethyl acetate and cold, aqueous sodium bicarbonate and the organic phase is separated. The organic phase is washed with saturated, aqueous sodium chloride, dried (MgSO$_4$), filtered, and evaporated to give a dark, semi-solid residue. Purification by PLC [1 development CH$_2$Cl$_2$—EtOAc (30:1)] provides 57.1 mg (41%) of seco-lactam 3, as a light yellow oil; IR(CHCl$_3$) 1760 (broad), 1715 (sh), and 1670 cm$^{-1}$; NMR (CDCl$_3$) δ:1.44 (d, J=6 Hz, 3H), 1.98 (S, 3H), 2.22 (S, 3H), 3.56 (dd, J=2.2, 7 Hz, 1H), 5.2 (m, 1H), 5.25 (dd, J=14 Hz, 2H), 5.3 (dd, J=13 Hz, 2H), 5.92 (d, J=2.2 Hz), 7.26 (S, 5H), 7.46 (m, 5H), 7.86 (d, J=8 Hz), and 8.16 (d, J=8 Hz); mass spectrum (FD) m/e 618(M+).

Step C:

To a stirred solution of 22.3 mg (0.036 mmoles of azetidinone 3 in 0.75 ml. of 8:1 acetone-water and two drops of 0.1 N pH 7 phosphate buffer at 25° C. is added all at once 5.7 mg (0.036 mmoles) of potassium permanganate. The mixture is stirred at 25° C. under nitrogen for 8 min and then an additional 5.7 mg of potassium permanganate is added. The mixture is stirred further for 50 min. and is then cooled on an ice-water bath, diluted with ethyl acetate, and is treated with 5% aqueous sodium thiosulfate. The mixture is filtered through celite and is washed well with ethyl acetate. The filtrate is partitioned between ethyl acetate and cold, aqueous brine solution and the organic phase is separated, dried (MgSO$_4$), filtered, and evaporated. The residue is purified by PLC [1 development CHCl$_3$—EtOAc (3:1)] to give 8.5 mg (55%) of azetidinone 4 as a colorless foam; IR(CHCl$_3$) 3375, 1760 (br), and 1660 CM$^{-1}$; NMR (CDCl$_3$) δ:1.51 (d, J=6 Hz, 3H), 3.52 (dd, J=2.2 and 7 Hz), 5.3 (m, 1H); 5.3 (dd, J=13 Hz, 2H), 5.5 (d, 2.2 Hz), 6.42 (bs, 1H), 7.51 (appt, J=8.0 Hz, 2H), 7.56 (d, J=9 Hz, 2H), 7.66, (appt., J=8.0 Hz, 1H), 7.92 (d, J=8.5 Hz), and 8.23 (d, J=9 Hz, 2H).

Step D:

A stirred mixture of 11.8 mg (0.027 mmoles) of azetidinone 4 (Step C) and a large excess of p-nitrobenzylglyoxalate hydrate in 1 ml of toluene and 0.5 ml of dimethylformamide containing 500 mg of ground 3 A molecular sieves is heated at 80° C. under a nitrogen atmosphere for 5.0 hr. The cooled mixture is diluted with ethyl acetate and is filtered. The filtrate is concentrated on a rotatory evaporator and the concentrate is partitioned between diethyl ether and cold water. The organic phase is separated, washed further with water, dried (MgSO$_4$), filtered, and evaporated. The residue is purified by PLC [1 development CHCl$_3$—EtOAc (3:1)] to give 5.0 mg (29%) of product 5; IR(CHCl$_3$): 3500, 1775, 1750, and 1665 cm$^{-1}$.

Step E:

To a stirred solution of 12.8 mg (0.02 mmoles) of lactam 5 from Step D in 1.0 ml anhydrous tetrahydrofuran at 0° C. under a nitrogen atmosphere is added in rapid succession 2.4 mg (0.02 mmoles) of neat thionyl chloride and 2.0 mg (0.02 mmoles) of neat triethylamine. The mixture is stirred at 0° C. for 2.0 hours and is then partitioned between diethyl ether and cold, aqueous brine. The organic phase is separated, washed with saturated, aqueous sodium chloride, dried (MgSO$_4$), filtered, and evaporated. The residue so obtained is dissolved in 0.5 ml dry tetrahydrofuran and is stirred with 10.0 mg (0.04 mmoles) of triphenylphosphine at 50° C. under a nitrogen atmosphere for 18.0 hrs. The cooled mixture is partitioned between ethyl acetate and aqueous sodium bicarbonate solution. The organic phase is separated, dried (Na$_2$SO$_4$), filtered, and evaporated. Purification of the residue by PLC affords the phosphorane derivative 6.

Step F:

A stirred solution of 88.3 mg (0.1 mmole) of phosphoraneazetidinone (Step E) in 80 ml of toluene is heated at 85° C. under an atmosphere of nitrogen for 3.5 days. The toluene is removed under reduced pressure and the residue is purified by plate layer chromatography to provide penem 7.

Step G:

A mixture of 60.5 mg (0.1 mmoles) of penem 7, 150 mg of 10% palladium-on-charcoal, and dilute, aqueous sodium bicarbonate in 5 ml. of ethyl acetate is hydrogenated at 25° C. and atmospheric pressure for 30 minutes. After this time 25 mg of fresh catalyst is added and the mixture is hydrogenated for an additional 5 minutes. The catalyst is removed by filtration and washed with dilute, cold aqueous sodium bicarbonate and ethyl acetate. The organic phase is separated and the aqueous phase acidified with dilute, cold aqueous citric acid. Thorough extraction of the acidified aqueous phase with methylene chloride, followed by drying (Na$_2$SO$_4$) and evaporation, provides the penem carboxylic acid 8, which is immediately converted to its sodium salt by treatment with a stoichiometric amount of aqueous sodium bicarbonate in acetone solution, evaporation of acetone, and lyopholization of the aqueous solution.

EXAMPLE 17A

Preparations of:

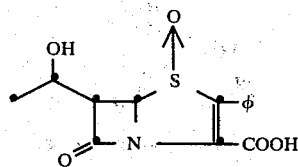

To a stirred solution of 60.5 mg (0.1 mmoles) of penem 7 from Example 17, step F in 2 ml of methylene chloride at 25° C. is added 20.3 mg (0.1 mmoles) of 85% m-chloroperbenzoic acid. The mixture is stirred at 25° C. under a nitrogen atmosphere for 0.5 hours and is then partitioned between methylene chloride and cold, dilute aqueous sodium bicarbonate. The organic phase is separated, dried ($Na_2SO_4$), filtered and evaporated to yield the desired sulfoxide.

The above illustrated carboxylic acid is obtained as described in Step G of Example 17 when the indicated substitution is made by catalytic hydrogenation of the sulfoxide prepared above.

EXAMPLE 18

Following the procedures described in the foregoing Examples and text, there is obtained the following species of the present invention by analogy:

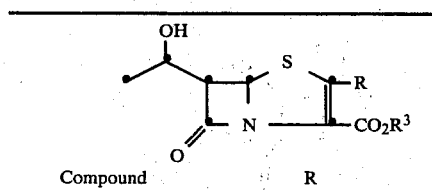

| Compound | R | $R^3$ |
|---|---|---|
| (1.) | $SCH_2CH_3$ | H |
| (2.) |  | H |
| (3.) |  | H |
| (4.) |  | H |
| (5.) |  | H |
| (6.) |  | H |
| (7.) |  | H |
| (8.) | $CH_3$ | Na |
| (9.) |  | Na |
| (10.) |  | H |
| (11.) | 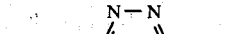 | H |
| (12.) | 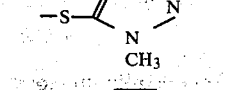 | H |

-continued

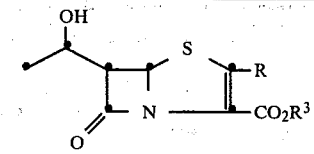

| Compound | R | $R^3$ |
|---|---|---|
| (13.) | 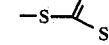 | H |
| (14.) | $-SCH_2CH_2OCCH_3$ (with C=O) | H |
| (15.) | $-SCH_2CH_2OH$ | H |
| (16.) |  | H |
| (17.) | $-SCH_2NH_2$ | H |
| (18.) | 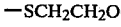 | H |
| (19.) | 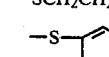 | H |
| (20.) |  | H |
| (21.) | 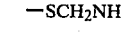 | Na |
| (22.) | 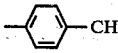 | Na |

EXAMPLE 19

Preparation of Pharmaceutical Compositions

One such unit dosage form is prepared by mixing 120 mg. of 6-(1'-hydroxyethyl)-2-methylthio-pen-2-em-3-carboxylic acid with 20 mg. of lactose and 5 mg of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 6-(1'-hydroxyethyl)-2-methylthio-pen-2-em-3-carboxylic acid | 125 mg. |
| Dicalcium Phosphate | 192 mg. |
| Cornstarch, U.S.P. | 6 mg. |
| Lactose, U.S.P. | 190 mg. |
| Magnesium Stearate | balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 6-(1'-hydroxyethyl)-2-methylthio-pen-2-em-3-carboxylic acid | 500 mg. |
| Diluent: Sterile Water for Injection | 2 cc |
| OPHTHALMIC SOLUTION | |
| 6-(1'-hydroxyethyl)-2-methylthio-pen-2-em-3-carboxylic acid | 100 mg. |
| Hydroxypropylmethyl cellulose | 5 mg. |
| Sterile Water | to 1 ml. |
| OTIC SOLUTION | |
| 6-(1'-hydroxyethyl)-2-methylthio-pen-2-em-3-carboxylic acid | 100 mg. |
| Benzalkonium chloride | 0.1 mg |
| Sterile Water | to 1 ml. |
| TOPICAL OINTMENT | |
| 6-(1'-hydroxyethyl)-2-methylthio-pen-2-em-3-carboxylic acid | 100 mg |
| Polyethylene Glycol 4000 U.S.P. | 400 mg |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A process for preparing a compound having the structure:

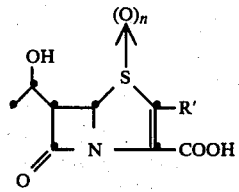

and the pharmaceutically acceptable salts thereof; wherein R' is hydrogen, —R, —OR, —SR, —NR$_2$; wherein R is substituted and unsubstituted: alkyl, having 1–6 carbon atoms, phenyl, phenylalkyl having 7–12 carbon atoms, heterocyclyl and heterocyclylalkyl wherein the alkyl has 1–3 carbon atoms and the heterocycle has 1–4 hetero atoms selected from O, N, and S; and wherein the chain or nuclear substituent on R is selected from amino, mono-, di- and trialkylamino (each alkyl having 1–6 carbon atoms), hydroxyl, alkoxyl, having 1–6 carbon atoms, mercapto, alkylthio having 1–3 carbon atoms, phenylthio, sulfamoyl, amidino, guanidino, nitro, chloro, bromo, fluoro, cyano, and carboxyl; n is 0 or 1; when n=1, R' is not —SR; comprising the steps of oxidizing:

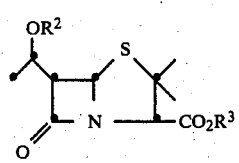

to form:

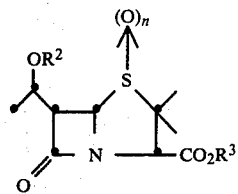

followed by treating with a phosphine in the presence of the anhydride (R$^3$CO)$_2$O to form:

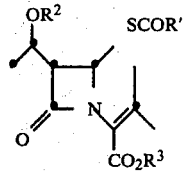

followed by oxidizing to form:

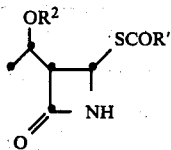

followed by treating with a glyoxalate ester to form:

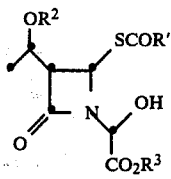

followed by halogenating to form:

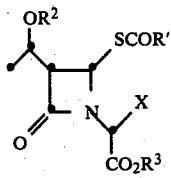

wherein X is halo; followed by treating with triphenylphosphine to form:

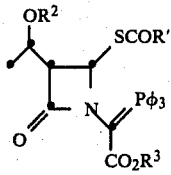

followed by cyclizing:

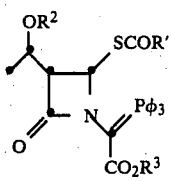

by heating, followed by deblocking; wherein R$^2$ is a readily removable protecting group; R$^3$ is a readily removable protecting group; and φ is phenyl.

* * * * *